United States Patent
Zapf et al.

(10) Patent No.: US 7,166,271 B2
(45) Date of Patent: Jan. 23, 2007

(54) SILICA-COATED BOEHMITE COMPOSITES SUITABLE FOR DENTIFRICES

(75) Inventors: Jason T. Zapf, Perryville, MD (US); William C. Fultz, Rising Sun, MD (US); Sung-Tsuen Liu, Aberdeen, MD (US); Mark E. Wozniak, Bel Air, MD (US)

(73) Assignee: J.M. Huber Corporation, Edison, NJ (US)

( * ) Notice: Subject to any disclaimer, the term of this patent is extended or adjusted under 35 U.S.C. 154(b) by 299 days.

(21) Appl. No.: 10/695,280

(22) Filed: Oct. 28, 2003

(65) Prior Publication Data
US 2005/0089582 A1   Apr. 28, 2005

(51) Int. Cl.
*A61K 8/00* (2006.01)
*A61K 8/18* (2006.01)
*A61Q 11/00* (2006.01)
*C01B 33/26* (2006.01)

(52) U.S. Cl. .................. 424/49; 423/328.1; 423/330.1; 501/128; 428/404

(58) Field of Classification Search ............... None
See application file for complete search history.

(56) References Cited

U.S. PATENT DOCUMENTS

| 2,885,366 | A |   | 5/1959  | Iler |
|-----------|---|---|---------|------|
| 2,913,419 | A |   | 11/1959 | Alexander |
| 4,708,945 | A | * | 11/1987 | Murrell et al. .............. 502/263 |
| 4,781,982 | A | * | 11/1988 | Musselman et al. ........ 428/403 |
| 4,826,430 | A |   | 5/1989  | Chen |
| 5,306,680 | A |   | 4/1994  | Fukuda |
| 5,340,393 | A |   | 8/1994  | Jacobson |
| 5,494,651 | A |   | 2/1996  | Minayoshi et al. |
| 6,048,577 | A |   | 4/2000  | Garg |
| 6,258,137 | B1 | * | 7/2001 | Garg et al. ................... 51/298 |

FOREIGN PATENT DOCUMENTS

| JP | 57-092519 A | 6/1982 |
| JP | 57-092520 A | 6/1982 |
| JP | 57-092521 A | 6/1982 |
| JP | 60-1666221 A | 8/1985 |
| JP | 04-238812 A | 8/1992 |

* cited by examiner

*Primary Examiner*—Frederick Krass
(74) *Attorney, Agent, or Firm*—David Mitchell Goodrich Carlos Nieves

(57) ABSTRACT

Disclosed is a composite material comprising a boehmite substrate coated with a precipitated silica, the composite having a BET specific surface area of from 1 $m^2/g$ to 50 $m^2/g$, such that the composite material has a % silica coating parameter value of about 5% to about 50%. Also disclosed is a dentifrice comprising this composite material. When included in a dentifrice composition, the composite material not only provides excellent abrasive and cleaning performance but also has compatibility with other ingredients used in dentifrice formulations, such as fluoride, flavors and cationic species.

21 Claims, No Drawings

SILICA-COATED BOEHMITE COMPOSITES SUITABLE FOR DENTIFRICES

BACKGROUND OF THE INVENTION

Boehmite (AlOOH) can be used as a dental abrasive to make dentifrice with low abrasivity and moderate cleaning ability, and is particularly well adapted for use with CPC, an antimicrobial agent frequently used in toothpaste formulations, because it has good CPC compatibility. However, boehmite also has the disadvantages of poor sodium fluoride compatibility and boehmite has also been known to negatively affect flavor ingredients. Additionally, boehmite provides relatively low abrasion levels thereby limiting its cleaning effectiveness.

Precipitated silica and silica gel are currently the preferred dental abrasives in dentifrices, since they have excellent sodium fluoride compatibility and can provide many levels of abrasiveness and cleaning ability depending on the silica structure chosen and the dentifrice loading level. However, these silicas have the disadvantages of poor compatibility with cationic antimicrobial ingredients such as CPC and are known to interact with dentifrice flavor components.

Thus, a dentifrice formulator striving to produce a dentifrice with high cleaning and low abrasivity, high CPC and sodium fluoride compatibility and reduced flavor interaction using a boehmite dental abrasive must balance several factors. While boehmite can be used at high loading levels to produce toothpaste that is effective at cleaning teeth with low abrasivity, the boehmite also negatively affects the compatibility with fluoride and interacts with flavorants to create off-flavors. So while adding boehmite provides cleaning benefits, its compatibility issues must be addressed before it can be effectively used in a dentifrice formulation.

Given the foregoing, there is a need for a boehmite composition that not only provides excellent abrasive and cleaning performance but also has compatibility with other ingredients used in dentifrice formulations, such as fluoride, flavors and cationic species.

BRIEF SUMMARY OF THE INVENTION

The present invention relates to a composite material comprising a boehmite substrate coated with a precipitated silica, the composite having a BET specific surface area of from 1 $m^2/g$ to 50 $m^2/g$, such that the composite material has a % silica coating parameter value of about 5% to about 50%.

The present invention also includes a dentifrice comprising about 10% to about 35% of the silica-coated boehmite a composite material.

The invention also includes a method of preparing a silica-coated boehmite comprising the steps of providing a boehmite slurry comprising boehmite particles; and precipitating a silica by adding an acid to an aqueous solution containing alkali metal silicate, thereby depositing silica, to form a composite which as a BET surface area of from 1 $m^2/g$ to 50 $m^2/g$ and the composite material having a % silica coating parameter value of about 5% to about 50%.

DETAILED DESCRIPTION OF THE INVENTION

All parts, percentages and ratios used herein are expressed by weight unless otherwise specified. All documents cited herein are incorporated by reference. The following describes preferred embodiments of the present invention, which provides a silica-coated boehmite composite material for use in dentifrices, such as toothpastes. While the optimal use for this silica-boehmite composite is in dentifrices, this silica-boehmite composite may also be used in a variety of other consumer products.

By "coated" it is meant that the specified coating ingredient covers at least a portion of the outer surface of a particle or substrate.

By "dense silica" it is meant nonporous amorphous silica having a reduced B.E.T. surface area.

By "mixture" it is meant any combination of two or more substances, in the form of, for example without intending to be limiting, a heterogeneous mixture, a suspension, a solution, a sol, a gel, a dispersion, or an emulsion.

When a material is said to be "silica treated", it is meant that the material is contacted by silica.

By "dentifrice" it is meant oral care products such as, without intending to be limiting, toothpastes, tooth powders, chewing gums and denture creams.

The present invention is directed to a silica-treated boehmite composite material, which, when included in a dentifrice composition, imparts excellent cleaning and abrasive characteristics as well as compatibility with therapeutic agents such as CPC when compared to prior art dental abrasives like precipitated silica. At the same time, because of the outer silica treatment (preferably in the form of a coating), the boehmite composite material has superior fluoride and flavor compatibility compared to prior art, untreated boehmite. These abrasive silica-boehmite composites not only clean teeth by removing debris and residual stains, but also function to polish tooth surfaces and are compatible with NaF and cationic species like cetyl pyridinium chloride (CPC).

This method of enhancing the cleaning ability and flavor and fluoride compatibility of boehmite by combining boehmite and silica ingredients to form a composite boehmite-silica material will now be discussed in greater detail. Subsequently, the ingredients themselves will be discussed in greater detail.

In summary, the method of preparing the inventive composite material involves a two step process: first, a slurry of boehmite particles is provided; and second, a precipitation reaction is created in order to precipitate a sufficient amount of the dense precipitated silica upon the substrate boehmite particulates to enhance the compatibility of the boehmite material to fluoride and flavor ingredients and maintain CPC compatibility, as described above.

In the first step of the method of preparing the inventive material involves first providing a source of boehmite material upon which to precipitate the precipitate dense-phase silica upon. Without intending to be limiting, this boehmite source is in slurry form obtained either by diluting dried, powdered, particulate boehmite with water to form a slurry; or using boehmite material that is already present in slurry or wet-cake form. In the latter case, the boehmite slurry or wet cake may be taken from an ongoing boehmite production run or stored as slurry or wet-cake without ever being dried to a powder or particulate form.

The boehmite particles, whether present in dried, powdered form or in a slurry preferably have a median particle size of about 1 μm to about 10 μm, a BET surface area of about 1 to 10 $m^2$ g, and a linseed oil absorption of about 30 to about 50 cc/100 g and a brass Einlehner value of about 10 to about 65 mg lost/100,000 revolutions. The boehmite particles are present in a slurry having a solids content of from about 10 to about 30%, by weight. (As used in the present invention, "slurry" is meant to include both a slurry and wet-cake forms).

In preferred embodiment the boehmite substrate particles are formed by the following process. First, an aqueous slurry containing about 10% to 30% solids of alumina trihydrate "ATH" particles is formed. The ATH slurry is heated in an agitated pressure reactor for about 30 to about 90 minutes under pressure from about 190 psi to about 250 psi, such as from about 200 psi to about 230 psi, to form boehmite. It should be noted that boehmite will form at pressures above 190 psi, however the upper pressure is limited to 250 psi for safety reasons. The boehmite particles formed are filtered and optionally washed to a filtrate conductivity of less than about 2000 µS/cm, such as from about 1 µS/cm to about 500 µS/cm, then optionally dried by any conventional means, such as spray drying.

The inventors have surprisingly discovered that the hardness of the formed boehmite particles is controlled by the amount of washing, with boehmite particles washed to a lower filtrate conductivity being harder, as measured by Einlehner abrasion. Also, it was discovered that the concentration of ATH solids in the reaction media affected the hardness of the formed boehmite particle, with lower solids concentration yielding more abrasive boehmite particles, as shown in the examples that follow.

After a slurry of boehmite particles is provided, a dense-phase amorphous precipitated silica coating, in a sufficient amount to enhance the compatibility of the boehmite material to fluoride and flavor ingredients, is applied to the boehmite particles by precipitating active silica in the reactor containing the boehmite-containing aqueous medium. The active silica is generated by acidulating an alkali metal silicate with a mineral acid therein, and the active silica thus generated is deposited as an amorphous silica precipitate material on the surfaces of the substrate boehmite particles. By active silica it is meant low molecular weight silica as defined by Iler in U.S. Pat. No. 2,885,366 [Iler], which is incorporated by reference.

The addition rates of the silicate and acid used for formation of active silica must be sufficiently slow in order to insure the active silica deposits on the existing substrate boehmite particles and does not form separate precipitated silica particles. The addition of active silica too rapidly will result in the formation of separate precipitated silica particles and will not result in the coating of the substrate boehmite. Generally, the dense silica coating formation takes about 60 min. to about 360 minutes. It is desirable to use temperatures ranging from about 60° C. to about 100° C., preferably from about 70° C. to about 95° C.; pH from about 7 to about 10, preferably from about 7 to about 9; and a dense silica deposition rate such that the surface area of the dense silica deposited on the boehmite substrate is about 1 $m^2/g$ to about 50 $m^2/g$, preferably from about 1 $m^2/g$ to about 35 $m^2/g$ and most preferably from 1 $m^2/g$ to about 10 $m^2/g$. Also, the dense silica deposited should be in an amount effective to reduce the binding of flavors and interaction of boehmite with sodium fluoride. The surface area of silica should be low enough to limit the interaction of the silica surface with flavorants and cationic species, like therapeutic agents such as CPC thereto in comparison to the silica particles with higher BET surface area. The reaction media may optionally contain an electrolyte, such as sodium sulfate.

The resulting mixture is gently agitated or mixed, such as with a paddle mixer, for a sufficient period of time to ensure that the boehmite particulates are substantially uniformly dispersed throughout the medium. The resulting silica-coated boehmite product is filtered or otherwise dewatered, washed, and dried as needed. Alternatively, the wet cake obtained can be reslurried, handled and supplied in slurry form.

Drying of the silica-coated boehmite described herein can be effected by any conventional equipment used for drying silica, e.g., spray drying, nozzle drying (e.g., tower or fountain), flash drying, rotary wheel drying or oven/fluid bed drying. The dried silica-coated boehmite product generally should have a 1 to 5 wt % moisture level, preferably less than 1.5%. Care must be taken that the drying operation and subsequent operations do not detrimentally affect the structure of the silica-coated boehmite obtained in the surface coating stage. Additionally, the silica-coated boehmite may be dried, collected and put through a second precipitation process to increase the percentage of silica coating, if desired.

To decrease the size of the dried surface-modified boehmite particles further, if desired, conventional grinding and milling equipment can be used. A hammer or pendulum mill may be used in one or multiple passes for comminuting and fine grinding can be performed by fluid energy or air-jet mill. Products ground to the desired size may be separated from other sizes by conventional separation techniques, e.g., cyclones, classifiers or vibrating screens of appropriate mesh sizing, and so forth.

In addition to the process described above, where boehmite substrate particles are first formed, and then in a second step, active silica is precipitated upon the boehmite particles, an alternative process exists in which the boehmite particles are produced in-situ, simultaneously with the precipitation reaction and the common silica coating operation. All of the relevant processing and composition parameters set forth above, are the same in this alternative process.

In order to meet the objectives of having high fluoride compatibility and high flavor compatibility, it is desired that the silica coated boehmite product generally has a coating of dense silica ranging from about 5% to about 50%, preferably from 15% to about 35%. The inventive silica-coated boehmite product generally has a sodium fluoride compatibility value of at least 15%, and particularly, can be greater than 50%, such as greater than 80%.

The 'Fluoride Compatibility' (also known as the 'Sodium Fluoride Compatibility') characteristic of the product is measured by a testing procedure explained in the examples that follow.

As discussed, the silica-coated boehmite also exhibits improved flavor compatibility. The flavor compatibility characteristic of the product is determined by a testing procedure explained in the examples that follow.

The inventive silica-coated boehmite product generally has a CPC Compatibility value of at least 55%, and more particularly, can be greater than 75%. The "CPC Compatibility" characteristic of the product is determined by a testing procedure explained in the examples that follow.

The resulting silica-coated boehmite also generally has a median particle size ranging between about 1 to about 20 microns, and preferably in one embodiment ranges between about 1 µm and about 12 µm. The particle size of the silica-coated boehmite is measured using a Model LA-910 laser light scattering instrument available from Horiba Instruments, Boothwyn, Pa.

The silica-coated boehmite composition may then be incorporated into a dentifrice composition, e.g., a toothpaste. Dentifrices that contain the above-described silica-coated boehmite product offer the benefit of relatively high cleaning and low abrasivity with improved compatibility with fluoride and CPC, and improved flavor attributes.

The silica-coated boehmite product does not accommodate the reaction of fluoride or the attachment CPC thereto. As a result, fluoride in the dentifrice is available to prevent the development and progression of dental caries. The CPC in the dentifrice also remains free and available for attachment to bacteria to which it comes into contact during oral cleaning.

As another benefit and advantage, dentifrices containing the silica-coated boehmite product have a superior flavor attributes. The flavor compatibility of the surface-treated boehmite product of this invention is superior to other dental abrasives like precipitated silicas, as has been demonstrated in experiments described herein.

Dentifrice Compositions

Dentifrices that contain the above-described low surface area silica-coated boehmite product offer the benefit that therapeutic agents, such as CPC, also can be used which remains at an effective antibacterial level in the dentifrice despite the presence of silica-coated boehmite abrasive. The low surface area silica-coated boehmite particles show decreased interaction with CPC and as a result there remains an increase in the free CPC in the dentifrice available to improve antibacterial efficacy.

While CPC is used herein as representative of dentifrice therapeutic agents, other antimicrobial agents, (cationic, anionic and nonionic) are contemplated by the invention. Other suitable antimicrobial agents include bisguariides, such as alexidine, chlorhexidine and chlorhexidine gluconate; quaternary ammonium compounds, such as benzalkonium chloride (BZK), benzethonium chloride (BZT), cetylpyridinium chloride (CPC), and Domiphen bromide; metal salts, such as zinc citrate, zinc chloride, and stannous fluoride; sanguinaria extract and sanguinarine; volatile oils, such as eucalyptol, menthol, thymol, and methyl salicylate; amine fluorides; peroxides and the like. Therapeutic agents may be used in dentifrice formulations singly or in combination. If present, the level of antibacterial agent is preferably from about 0.1 wt % to about 5 wt % of the toothpaste composition.

As another benefit and advantage, dentifrices containing the low B.E.T. surface area silica-coated boehmite product have a superior flavor attributes. The flavor compatibility of the low surface area silica-coated boehmite product of this invention is superior to a higher B.E.T. surface area silica materials, as has been demonstrated in experiments described herein.

Dentifrice compositions incorporating the low surface area silica-coated boehmite product described herein generally contain the silica-coated boehmite in an effective amount for abrasive and polishing action. This amount can vary, depending on other ingredients of the formulation, for example, but generally will range from about 5 to about 50 wt % such as about 10% to about 35%.

A water-soluble fluoride compound optionally can be added and present in dentifrices and other oral compositions in an amount sufficient to give a fluoride ion concentration in the composition at 25° C., and/or when it is used of from about 0.0025% to about 5.0% by weight, preferably from about 0.005% to about 2.0% by weight, to provide additional anticaries effectiveness. A wide variety of fluoride ion-yelding materials can be employed as sources of soluble fluoride in the present compositions. Examples of suitable fluoride ion-yelding materials are found in U.S. Pat. No. 3,535,421 and U.S. Pat. No. 3,678,154, both being incorporated herein by reference. Representative fluoride ion sources include stannous fluoride, sodium fluoride, potassium fluoride, sodium monofluorophosphate and many others. Stannous fluoride and sodium fluoride are particularly preferred, as well as mixtures thereof.

Flavoring agents optionally can be added to dentifrice compositions. Suitable flavoring agents include oil of wintergreen, oil of peppermint, oil of spearmint, oil of sassafras, and oil of clove, cinnamon, anethole, menthol, and other such flavor compounds to add fruit notes, spice notes, etc. These flavoring agents consist chemically of mixtures of aldehydes, ketones, esters, phenols, acids, and aliphatic, aromatic and other alcohols.

Sweetening agents which can be used include aspartame, acesulfame, saccharin, dextrose, levulose and sodium cyclamate. Flavoring and sweetening agents are generally used in dentifrices at levels of from about 0.005% to about 2% by weight.

Other additives commonly used or otherwise beneficial in dentifrices also optionally may be included in the formulation. A pharmaceutically acceptable carrier for the components of dentifrice compositions containing silica-coated boehmite product of the present invention is optional and can be any dentifrice vehicle suitable for use in the oral cavity. Such carriers include the usual components of toothpastes, tooth powders, prophylaxis pastes, lozenges, gums, and the like and are more fully described thereafter.

Water is also present in the toothpastes and dentifrices according to another embodiment of this invention. Water employed in the preparation of suitable toothpastes should preferably be deionized and free of organic impurities. Water generally comprises from about 2% to 50%, preferably from about 5% to 20%, by weight, of the toothpaste compositions. These amounts of water include the free water, which is added plus that which is introduced with other additives and materials, such as humectant.

In preparing toothpastes, it often is necessary to add some thickening or binder material to provide a desirable consistency and thixotropy. Preferred thickening agents are carboxyvinyl polymers, carrageenan, hydroxyethyl cellulose and water-soluble salts of cellulose ethers such as sodium carboxymethyl cellulose and sodium carboxymethyl hydroxyethyl cellulose. Natural gums such as gum karaya, xanthan gum, gum arabic, and gum tragacanth can also be used. Thickening agents in an amount from about 0.5% to about 5.0% by weight of the total composition generally can be used.

Silica thickeners can also be used to modify toothpaste rheology. Precipitated silica, silica gels and fumed silica can be used. Silica thickeners can be added generally at a level of about 5% to about 15%.

It is also often desirable to include some humectant material in a toothpaste to keep it from hardening. Suitable humectants include glycerin (glycerol), sorbitol, polyalkylene glycols such as polyethylene glycol and polypropylene glycol, hydrogenated starch hydrolyzates, xylitol, lactitol, hydrogenated corn syrup, and other edible polyhydric alcohols, used singly or as mixtures thereof. Suitable humectants can be added generally at a level of from about 15% to about 70%.

Chelating agents optionally can be added to the dentifrices of the invention, such as alkali metal salts of tartaric acid and citric acid, or alkali metal salts of pyrophosphates or polyphosphates.

Other optional ingredients and adjuvants of dentifrices, such as those described in U.S. Pat. No. 5,676,932 and Pader, M., Oral Hygiene Products and Practice, Marcel Dekker, Inc., New York, 1988, for instance, also can be added as needed or desired. These other optional adjuvants, additives, and materials that can be added to the dentifrice compositions of the present invention include, for example, foaming agents (e.g., sodium lauryl sulfate), detergents or surfactants, coloring or whitening agents (e.g., titanium dioxide, FD&C dyes), preservatives (e.g., sodium benzoate, methyl paraben), chelating agents, antimicrobial agents, and other materials that can be used in dentifrice compositions. The optional additives, if present, generally are present in small amounts, such as no greater than about 6% by weight each.

Additionally, while the usefulness of the abrasive cleaning material of this invention is specifically illustrated in oral cleaning compositions, it is will be appreciated that the surface-modified boehmite of this invention has wider usefulness. For instance, it can be used in metal, ceramic or porcelain cleaning or scrubbing.

The invention will now be described in more detail with respect to the following, specific, non-limiting examples. In the following examples, parts are by weight unless indicated otherwise.

As a first step, the boehmite substrate was prepared. Three batches of boehmite (Example A, B, and C) were used to prepare Examples 1–4 of silica-coated boehmite as described below.

EXAMPLE A

Two batches of alumina trihydrate (ATH) slurry were prepared and combined, since the mixing tank used was smaller than the reactor used, by mixing under agitation 200 lbs. (90.7 kg) Micral® 9400 ATH with 393 lbs. (178.3 kg) of water and adding this slurry to a 300-gal. Pressure reactor. Then 223 lbs. (101.2 kg) Micral® 9400 ATH was mixed with 443 lbs. (200 kg) water and added to the same reactor. Micral® 9400 ATH is available from J.M. Huber Corporation. The tank used to prepare both ATH slurries was rinsed with 23 liters of water and the rinse water added to the reactor. The reactor solids content was about 32–33%. The reactor agitator speed was set to 270 RPM and the reactor was heated from atmospheric pressure to 190–200 psi with live steam injection, which took about 60 min. Once this pressure was reached, it was maintained with live steam for 60 minutes reaction time. After the 60-minute reaction time, the reactor was vented to a pressure of 30 psi. Thereafter, the formed boehmite was unloaded from the reactor into a drop tank containing enough water to cover the mixing blade, then conveyed to a rotary filter and filtered and washed to a filtrate conductivity of about 100 μS. The wet cake was slurried in water to about 30–35% solids and then feed into a spray drier at a feed rate of 3.0 l/min and spray dried at an outlet temperature of 120° C. and an inlet temperature of about 400° C.

EXAMPLE B

The same procedure as used to produce Example A was followed, except the filter cake was washed to a filtrate conductivity of about 400 μS.

EXAMPLE C

The procedure of Example A was followed except less water was used in the ATH slurrying steps giving a initial higher solids content in the reactor (34–35% vs. 32–33% in Example A) and the agitator speed was set to 220 RPM, instead of the 270 RPM as in Example A. Specifically, in this example the same two weights of ATH as in Example A were used with 371.4 lbs. (168.5 kg) and 394.9 lbs. (179.1 kg) of water, respectively.

Properties of the prepared boehmite Examples A–C are summarized in Table II below.

EXAMPLES D–F

Next, several laboratory scale batches of boehmite were prepared in a 2-gallon Parr reactor equipped with an agitator and temperature controls. A slurry of Micral 9400 ATH and water was added to the reactor and heated to a reaction temperature within 90 minutes. The agitator was set to an rpm speed and the reaction media digested for a digest time. Thereafter the Parr reactor was cooled, vented and the boehmite was recovered by filtration on a buchner funnel and optionally washed with a number of water displacements. The boehmite filter cake was dried overnight at 105° C. Process parameters and boehmite properties are provided in Table A. Boehmite properties were measured using the methods described below following the examples.

TABLE A

|  | Ex. D | Ex. E1 | Ex. E2 | Ex. F1 | Ex. F2 |
|---|---|---|---|---|---|
| ATH, g | 1750 | 1267 | 1267 | 670.6 | 670.6 |
| $H_2O$, g | 5250 | 3800 | 3800 | 3800 | 3800 |
| % Solids | 25 | 25 | 25 | 15 | 15 |
| Heating Temp, ° C. | 195 | 200 | 200 | 200 | 200 |
| RPM | 250 | 600 | 600 | 600 | 600 |
| Digest Time, min | 60 | 30 | 30 | 30 | 30 |
| Wash displacements | 1 | 0 | 2 | 0 | 2 |
| Filtrate Conductivity, μS/cm | — | 1700 | 16 | 1520 | 7 |
| Einlehner, mg lost | 27.7 | 9.1 | 44.6 | 16.7 | 62.8 |
| Oil absorption, ml/100 g | 35 | 48 | 46 | 38 | 45 |
| Median particle size, μm | 2.3 | 1–3 | 1–3 | 1–3 | 1–3 |
| BET, $m^2/g$ | 4 | 4 | 4 | 5 | 5 |
| 5% pH | 8.7 | 9.45 | 6.63 | 9.36 | 5.83 |

It is shown in the table above that the hardness of boehmite represented by the Einlehner abrasion value is proportional to the amount of washing and inversely proportional to the reaction % solids concentration.

EXAMPLES 1–4

In a steam jacketed 30-gallon reactor equipped with a recirculating loop, an inline pH electrode and a stirring device, was added a specified volume of $H_2O$ and weight of boehmite. The recirculation pump was started and the reaction media was heated to reaction temperature with constant stirring at 200 rpm. The recirculation pump, reaction temperature and agitation rate was maintained for the duration of batch. Then sodium silicate (13.0%, 3.3 molar ratio $SiO_2:Na_2O$, S.G. 1.112) and 11.4% $H_2SO_4$ were added simultaneously to the reactor contents at specified rates. Simultaneous addition was continued for a specified time while maintaining a specified pH. The sulfuric acid rate was adjusted as necessary to maintain pH while keeping the sodium silicate rate constant throughout. After the specified time, the silicate addition was stopped while acid addition continued until the final pH was reached. Thereafter, the batch was digested at the same batch temperature, after which the pH was readjusted to the final pH with sulfuric acid. The resultant product was filtered using a plate and frame filter press while washing to a conductivity of <1500 μS. The press cake was slurried in water to 10–36% solids and spray dried (S.D.). Alternately, the press cake was dried overnight (about 14–18 hrs.) in an oven set at 105° C. The process variables for Examples 1–4 are provided in Table I and the properties of Examples 1–4 silica-coated boehmite are given in Table II below.

TABLE I

Process Conditions

|  | Example 1 837-60-2 | Example 2 837-2-1 | Example 3 837-43-1 | Example 4 837-81-1 |
|---|---|---|---|---|
| Boehmite source | Ex. A | Ex. B | Ex. B | Ex. C |
| $H_2O$ vol., liters | 72.0 | 72.0 | 45.0 | 23.0 |
| Boehmite wt., kg | 8.0 | 8.0 | 11.25 | 9.85 |
| Reaction temp., ° C. | 80 | 80 | 75 | 75 |
| Simultaneous addition |  |  |  |  |
| Sodium silicate rate, ml/min | 71.3 | 71.3 | 104.7 | 198.1 |
| Acid rate, ml/min | 29.0 | 29.0 | 38.9 | 87.7 |
| Reaction pH | 8.0 | 8.0 | 9.0 | 7.0 |
| Time, min. | 180 | 180 | 325.6 | 243.5 |
| Final pH | 5.5 | 5.5 | 7.0 | 5.0 |
| Digestion time, min. | 10 | 10 | 0 | 0 |
| Dryer type | S.D. | S.D. | Oven | Oven |

EXAMPLE 5

A 10% slurry of boehmite containing 600 g of Example D boehmite and 5400 ml water was added to a 2-gallon reactor. The reaction media was heated to 80° C. with constant stirring at 400 rpm. Sodium silicate (3.3 mole ratio, (3.0%) and 11.4% sulfuric acid were added simultaneously for 180 minutes at rates of 5.4 ml/min and 2.2 m/min, respectively. The pH was maintained at 8.0±0.2 by adjusting the acid rate as necessary. At the end of 180 minutes, sodium silicate addition was stopped and the acid addition was continued until the pH reached 5.5±0.2. Thereafter the batch was digested for 10 minutes, then filtered and washed with one displacement of deionized water. The silica-coated boehmite product was oven dried at 105° C. overnight. Example 5 product properties are summarized below in Table II.

COMPARATIVE EXAMPLE 1

Boehmite coated with 0.2% silica was made following the conditions outlined in U.S. Pat. No. 4,781,982. 400 g of 1% sodium silicate (0.115 mole ratio) was mixed at 400 rpm with 200 g boehmite of Example C. To this slurry, 0.2N hydrochloric acid was added at a rate of 5.9 ml/min for about 1 hour to a final pH of 6.0. The slurry was then filtered and washed with de-ionized water. The resulting product was dried at 105° C. in an oven.

After being prepared as set forth above, several properties of the particulate silica-coated boehmite material, including % silica coating, Einlehner abrasion, oil absorption, particle size, surface area, 5% pH, % sodium fluoride compatibility, % cetylpyridinium chloride (CPC) compatibility, and flavor compatibility were measured.

The "% Silica Coating" values, as used herein in the description and claims were determined by calculation from the batch parameters. The Silica coating level is determined by knowing the weight of active silica used and the silicate concentration, S.G. and M.R. the % Silica coating is calculated by taking the weight Active Silica divided by total weight times 100.

An example calculation for Example 1 is as follows:
Silicate used is 13%, 3.32 M.R., 1.112 S.G.

weight active silica=(71.3 ml/min) (180 min) (0.13) (1.112) (3.32) (60/261.2)=1414 g $SiO_2$
weight substrate=8 kg=8000 g
% silica coating=1414/(1414+8000)×100=15%

The Brass Einlehner (BE) Abrasion value was measured through the use of an Einlehner AT-1000 Abrader. In this test, a Fourdrinier brass wire screen is weighed and exposed to the action of a 10% aqueous abrasive suspension for a fixed number of revolutions, and the amount of abrasion is then determined as milligrams brass lost from the Fourdrinier wire screen per 100,000 revolutions. Disposable supplies required for this test (brass screens, wear plates and PVC tubing) are available from Duncan Associates, Rutland, Vt. and sold as an "Einlehner Test Kit". Specifically, brass screens (Phosphos Bronze P.M.) were prepared by washing in hot, soapy water (0.5% Alconox) in an ultrasonic bath for 5 minutes, then rinsed in tap water and rinsed again in a beaker containing 150 ml water set in an ultrasonic bath. The screen is rinsed again in tap water, dried in an oven set at 105° C. for 20 minutes, cooled in a desiccator and weighed. Screens were handled with tweezers to prevent skin oils from contaminating the screens: The Einlehner test cylinder is assembled with a wear plate and weighed screen (red line side down—not abraded side) and clamped in place. The wear plate is used for about 25 tests or until worn badly; the weighed screen is used only once.

A 10% abrasive slurry, prepared by mixing 100 g abrasive with 900 g deionized water, was poured into the Einlehner test cylinder. Einlehner PVC tubing was placed onto the agitating shaft. The PVC tubing has 5 numbered positions. For each test, the position of the PVC tubing is incremented until it has been used five times, then discarded. The Einlehner abrasion instrument is re-assembled and the instrument set to run for 87,000 revolutions. Each test takes about 49 minutes. After the cycle is completed, the screen is removed rinsed in tap water, placed in a beaker containing water and set in an ultrasonic bath for 2 minutes, rinsed with deionized water and dried in an oven set at 105° C. for 20 minutes. The dried screen is cooled in a desiccator and reweighed. Two tests are run for each sample and the results are averaged and expressed in mg lost per 100,000 revolutions. The result, measured in units of mg lost per 100,000 revolutions, for a 10% slurry can be characterized as the 10% brass Einlehner (BE) abrasion value.

The oil absorption was measured using linseed oil by the rubout method. In this test, oil is mixed with a test sample and rubbed with a spatula on a smooth surface until a stiff putty-like paste is formed. By measuring the quantity of oil required to have a paste mixture, which will curl when spread out, one can calculate the oil absorption value of the sample—the value which represents the volume of oil required per unit weight of sample to completely saturate the sample sorptive capacity. Calculation of the oil absorption value was done as follows:

$$\text{Oil absorption} = \frac{\text{ml oil absorbed}}{\text{weight of sample, grams}} \times 100$$

$$= \text{ml oil}/100 \text{ gram sample}$$

The Median Particle Size (MPS) is determined using a Model LA-910 laser light scattering instrument available from Horiba Instruments, Boothwyn, Pa. A laser beam is projected through a transparent cell, which contains a stream of moving particles suspended in a liquid. Light rays striking the particles are scattered through angles which are inversely proportional to their sizes. The photodetector array measures the quantity of light at several predetermined angles. Electrical signals proportional to the measured light flux values are then processed by a microcomputer system to form a multi-channel histogram of the particle size distribution.

The Surface Area is determined by the BET nitrogen adsorption methods of Brunaur et al., *J. Am. Chem. Soc.*, 60, 309 (1938).

The 5% pH is determined by weighing 5.0 grams sample and 95 ml deionized or distilled water into a 250-ml beaker, mixing for 7 minutes on a magnetic stir plate, and measuring the pH with a pH meter, which has been standardized with two buffer solutions bracketing the expected pH range.

Sodium Fluoride Compatibility, as used herein in the description and claims, is determined by slurrying a sample for one week in a solution of sodium fluoride at a temperature of 140° F., and comparing the fluoride remaining in the supernatant with that in the original sodium fluoride solution. The supernatant and standards are dilutes 1:1 with EDTA/THAM solution, and the fluoride concentration is determined by direct potentiometry with the Orion Model EA-940 Multi-channel Benchtop Meter (Thermo Orion, Beverly, Mass.) using a fluoride electrode (Orion Fluoride-Specific Ion Combination Electrode, Model No, 96-09).

A sodium fluoride stock solution (1624 ppm F) is prepared by dissolving 2.80 g of 99.5% minimum purity sodium fluoride reagent (J. T. Baker, Phillipsburg, N.J.), 21.5 g $NaH_2PO_4.H_2O$ (Mallinckrodt Baker Inc., Phillipsburg, N.J.) and 83.4 g $Na_2HPO_4.2H_2O$ (Mallinckrodt Baker Inc., Phillipsburg, N.J.) in 672.5 g deionized or distilled water. Sodium fluoride stock solution is stored in a polyethylene bottle.

A 1:1 EDTA/THAM solution (0.2 N EDTA/0.2 N THAM solution; pH=8.0) is prepared using ethylene dinitrillo tetraacetic acid, disodium salt ($Na_2EDTA.2H_2O$), A.C.S. grade (Mallinckrodt Baker Inc., Phillipsburg, N.J.) and THAM (2-amino-2-(hydroxymethyl)-1,3-propanediol) (Matheson, Coleman & Bell, Gardena, Calif.). 5 N NaOH solution (NaOH pellets from Mallinckrodt Baker Inc., Phillipsburg, N.J.) is used to adjust the pH of the solution to 7.5–8.0.

Two fluoride standard calibration solutions were prepared, one high (1624 ppm fluoride) and one low (162.4 ppm fluoride), using sodium fluoride stock solution and EDTA/THAM solution.

The response of the fluoride electrode must be checked each time it is used in order to establish the potential response versus concentration of free fluoride. The High and Low Standard Calibration Solutions are used to check the response of the electrode and concentration measurement. The potential of the standardizing solutions and each test supernatant is read at room temperature (70–80° F.).

To prepare samples for testing, 30.0 grams of Sodium Fluoride Stock Solution (from the same batch of solution used to prepare the standards) is weighed into a centrifuge tube. 7.0 g of the test material is slowly added to the tube so that it forms a smooth slurry. The tube is tightly capped and mixed for one week at a temperature of 140° F. using a rotating rack. The sample is centrifuged for 20 minutes at 15,000 rpm or until the supernatant is clear. 10 ml of supernatant and 10 ml of EDTA/THAM Solution are pipetted into a plastic vial and stirred. The fluoride concentration in the sample is read on Orion Model EA-940 Multi-channel Benchtop Meter. Percent fluoride compatibility is calculated as follows:

$$\% \text{ Fluoride Compatibility} = \frac{\text{ppm } F \text{ in sample}}{1624} \times 100$$

Cetylpyridinium Chloride (CPC) Compatibility, as used herein in the description and claims, was measured as follows.

27.00 g of a 0.3% solution of CPC was added to a 3.00 g sample of the silica to be tested. The silica was previously dried at 105° C. to 150° C. to a moisture content of 2% or less, and the pH of the sample was measured to ensure the 5% pH was between 5.5 and 7.5. The mixture was shaken for a period of 10 minutes. Accelerated aging testing requires agitation of the test specimen for 1 week at 140° C. After agitation was complete, the sample was centrifuged and 5 ml of the supernatant was passed through a 0.45 μm PTFE milli-pore filter and discarded. An additional 2.00 g of supernatant was then passed through the same 0.45 μm PTFE milli-pore filter and then added to a vial containing 38.00 g of distilled water. After mixing, an aliquot of the sample was placed in a cuvette (methyl methacrylate) and the U.V. absorbance was measured at 268 nm. Water was used as a blank. The % CPC Compatibility was determined by expressing as a percentage the absorbance of the sample to that of a CPC standard solution prepared by this procedure with the exception that no silica was added.

TABLE II

|  | % Silica Coating | Einlehner abrasion (mg lost) | Oil Absorption (ml/100 g) | Median Particle Size (μm) | BET Surface Area (m²/g) | 5% pH | % NaF Compatibility | % CPC Compatibility |
|---|---|---|---|---|---|---|---|---|
| Example 1 | 15 | 16.7 | 63 | 2.4 | 4 | 8.7 | 42 | 74.7 |
| Example 2 | 15 | 29.4 | 47 | 3.0 | 5 | 8.4 | 20 | — |
| Example 3 | 25 | 22.8 | 53 | 11.0 | 8 | 9.6 | 84 | 55.7 |
| Example 4 | 35 | 21.0 | 66 | 6.9 | 6 | 7.0 | 91 | 81.6 |
| Example 5 | 15 | 23.1 | 52 | 3.1 | 5 | 8 | 80 | — |
| Zeodent ® 115 silica | NA | 3.7 | 95 | 9.8 | 52 | 7.2 | 96 | <2.0 |
| Comparative Example 1 | 0.2 | — | 47 | 1.4 | 3 | 9.2 | 12 | — |
| Ex. A boehmite | 0 | 22 | 37 | 1.4 | 3 | 9.2 | 17 | 96.3 |
| Ex. B boehmite | 0 | 33.6 | 36 | 1.9 | 2 | 8.5 | 14 | 99.3 |
| Ex. C boehmite | 0 | 19.4 | 37 | 1.4 | 3 | 9.4 | 18 | 95.8 |

As can be seen in Table II, the silica-coated boehmite samples prepared in Examples 1–5 have improved fluoride compatibility over the untreated boehmite materials while maintaining a CPC compatibility that is much better than that of traditional precipitated silica, illustrated by Zeodent® 115 silica available from J.M. Huber Corporation. The 0.2% silica-coated boehmite of Comparative Example 1 yielded poor fluoride compatibility providing no improvement over the uncoated starting boehmite.

The flavor compatibility of Example 1, 3–4 silica-coated boehmite was compared to that of untreated boehmite and prior art Zeodent® 115 precipitated silica. Flavor Compatibility is determined by GCMS according to the following procedure:

Sample Preparation:

0.5 g of a test material was weighed to 2 decimal place accuracy and loaded into 15 ml amber glass screw top with polypropylene hole cap vials w/PTFE/Silicone septa (available from Supelco, Bellefont, Pa., part # 27049,). Using a gas tight syringe, 10 µl of a Natural Spearmint Essential Oil (Available from Sigma Aldrich, St. Louis, Mo., Cat. # W30322-4,) was added to the samples, taking care to evenly distribute the oil on the sample, and not to wet the inside of the glass vial with the oil. The vials were then capped and the samples agitated on a vortex mixer for approximately 10 seconds to ensure even distribution of the oil on the sample. The samples were allowed to equilibrate for at least several hours at room temperature, such as overnight and then tested at 22.5–23.5° C. The samples were not agitated immediately prior to analysis. Two specimens were tested for each sample and the results averaged.

Headspace Sampling

The samples were then sampled for 5 minutes at room temperature using a 65 µm Polydimethylsiloxane-Divnylbenzene Solid Phase microextraction (SPME) fiber (available from Supelco, #57310-U) and a manual fiber holder assembly (Supelco #57330-U). Room temperature was maintained between 22.5 and 23.5C during the analysis. After a 5 minute exposure, the fiber was withdrawn from the sample vial and desorbed into the GCMS system and analyzed under the following conditions.

Chromatography Conditions:

A Hewlett Packard 5890 GC with 5972 Mass Selective Detector was used for this analysis.

Column: Restek Stabilwax, 60 m, 0.25 mmID, 0.25 µm film (Restek Corp., Bellefont, Pa.)
Injection: 250° C., 25 ml/min split, 1 mm split liner
Carrier: He 28 cm/sec @ 100° C.
Oven Program:
50° C., hold 4 minutes
4° C./min to 100° C., hold 0 minutes
8° C./min to 200° C., hold 0 minutes
25° C./min to 240° C., hold 4 minutes
Detector: MS 280C, scan mode, 30–550AMU.

The oil of spearmint reference was prepared in the same manner as described above, except without the addition of any test material. Ten of the major oil of spearmint constituent peaks were chosen for data collection to evaluate the effect of different test materials on the intensity of these flavor components. It is theorized that a change in peak intensity of some of the flavor components is proportional to changes in perceived flavor.

TABLE III

Flavor Oil Component Intensity

| Peak ID | Std. Oil Peak Area $\times 10^{-4}$ | Ex. 1 Peak Area $\times 10^{-4}$ | Ex. 3 Peak Area $\times 10^{-4}$ | Ex. 4 Peak Area $\times 10^{-4}$ | Zeodent 115 Silica Peak Area $\times 10^{-4}$ | Ex. A boehmite Peak Area $\times 10^{-4}$ |
|---|---|---|---|---|---|---|
| a-pinene | 1053 | 961 | 937 | 1013 | 635 | 1001 |
| b-pinene | 996 | 931 | 917 | 981 | 637 | 960 |
| myrcene | 2798 | 2574 | 2526 | 2735 | 1610 | 2627 |
| limonene | 16594 | 15787 | 15657 | 16804 | 11656 | 15783 |
| eucalyptol | 2306 | 1838 | 1752 | 1870 | 61 | 2055 |
| 3-octanol | 646 | 453 | 410 | 503 | 6 | 358 |
| b-terpineol | 380 | 254 | 236 | 219 | 2 | 195 |
| menthone | 306 | 300 | 310 | 345 | 5 | 240 |
| Dihydrocarvone | 1118 | 1107 | 1242 | 1343 | 40 | 896 |
| carvone | 20306 | 20980 | 23570 | 24565 | 737 | 16859 |

Shown in Table IV below is the difference in flavor component intensity between each example and that of the standard oil for each of the examples given in Table III.

TABLE IV

% Difference from Standard Flavor Oil

| Peak ID | Ex 1 | Ex. 3 | Ex. 4 | Zeodent 115 Silica | Ex. A boehmite |
|---|---|---|---|---|---|
| a-pinene | −8.7 | −11.0 | −3.8 | −39.7 | −4.9 |
| b-pinene | −6.5 | −7.9 | −1.5 | −36.0 | −3.6 |
| myrcene | −8.0 | −9.7 | −2.2 | −42.4 | −6.1 |
| limonene | −4.9 | −5.6 | 1.3 | −29.8 | −4.9 |
| eucalyptol | −20.3 | −24.0 | −18.9 | −97.4 | −10.9 |
| 3-octanol | −29.8 | −36.5 | −22.1 | −99.1 | −44.5 |
| b-terpineol | −33.2 | −37.9 | −42.4 | −99.5 | −48.7 |
| menthone | −2.0 | 1.3 | 12.7 | −98.4 | −21.6 |
| dihydrocarvone | −0.9 | 11.1 | 20.2 | −96.4 | −19.8 |
| carvone | 3.3 | 16.1 | 21.0 | −96.4 | −17.0 |

As can be seen in Tables III and IV, the silica-coated boehmite prepared according to the present invention had much less effect than traditional silica (Zeodent 115) on the various major components of a typical toothpaste flavor. Silica-coated boehmite also had less effect than the untreated boehmite materials on the 3-octanol, b-terpineol, menthone, dihydrocarvone, and carvone components of this flavor.

To demonstrate their efficacy in consumer products, the silica-coated boehmite abrasives of Examples 1–5 were incorporated as powders into five different toothpaste compositions (numbers 1–5), which are set forth in Table V, below. The performance of these compositions was then compared with the performance of the following toothpaste compositions: compositions 6–7, which contain the untreated boehmite abrasives of Examples A and B, respectively; and composition 8, which contains a prior art silica abrasive (Zeodent® 115 available from J.M. Huber Corporation, Edison, N.J.).

These toothpaste compositions were prepared as follows. A first mixture was formed by combining the following components: glycerin, sorbitol, polyethylene glycol (Carbowax 600, from the Union Carbide Corporation, Danbury, Conn.), carboxymethylcellulose (CMC-7MXF, from the Aqualon division of Hercules Corporation, Wilmington, Del.), and then stirring the first mixture until the components dissolved. A second mixture was formed by stirring the following components together until dissolved: deionized water, tetrasodium pyrophosphate, sodium saccharin, sodium fluoride. The first and second mixtures were then combined while stirring to form a "premix".

The premix was placed in a Ross mixer (model 130LDM, Charles Ross & Co., Haupeauge, N.Y.), then Zeodent 165 silica thickener (J.M. Huber Corporation), titanium dioxide, and abrasive were added to the premix, and the premix mixed without vacuum. Then 30 inches of vacuum was drawn and each sample mixed for 15 minutes, and then sodium lauryl sulfate and flavor was added. The resulting mixture was stirred for 5 minutes at a reduced mixing speed. The prepared toothpaste compositions were placed in laminated toothpaste tubes and stored for evaluation of several properties. The different toothpaste compositions were prepared according to the following formulations, wherein the amounts are gram units:

After toothpaste compositions 1–8 were prepared as described above from the amounts of ingredients in Table V. Properties such as fluoride availability, RDA, and PCR were determined as follows.

To determine fluoride availability values for the toothpastes tested, a soluble fluoride determination method is used. In this method, toothpaste compositions were stored at a specified temperature for a specified length of time in a laminated tube. Thereafter, 10 grams of the toothpaste composition was placed in a 10-ml beaker and 45.0 grams of distilled water was added. The mixture was stirred to form a slurry in which the toothpaste was uniformly dispersed. The slurry was subsequently centrifuged for 10 minutes at 15,000 rpm or until the supernatant was clear. Then 10 ml of the supernatant and 5 ml of 2 molar perchloric acid was pipetted into a plastic vial. The vial was capped, mixed and allow to stand at room temperature for 24 hours. Then 25 ml of 1.5 molar sodium citrate buffer was pipetted into the vial. (The sodium citrate buffer is prepared by dissolving 220.6 grams of sodium citrate in 500 ml of distilled water.) A magnetic stir bar was added and gentle stirring was initiated. The fluoride ion concentration was determined by direct potentiometry with an Orion fluoride electrode (Model 95-09).

The radioactive dentin abrasion (RDA) method used to analyze the toothpaste compositions is described by Grabenstetter, R. J.; Broge, R. W.; Jackson, F. L.; and Radike, A. W.: The Measurement of the Abrasion of Human Teeth by Dentifrice Abrasives: A Test Utilizing Radioactive Teeth, Journal of Dental Research 37: 1060–68, 1958.

The PCR test used to analyze the toothpaste compositions is described in "*In Vitro Removal of stain With Dentifrice*" G. K. Stookey, et al., J. Dental Res., 61, 1236–9, 1982.

TABLE V

| | Toothpaste Composition Number | | | | | | | |
| --- | --- | --- | --- | --- | --- | --- | --- | --- |
| | 1 | 2 | 3 | 4 | 5 | 6 | 7 | 8 |
| Glycerin, 99.5% | 11.000 | 11.000 | 11.000 | 11.000 | 11.000 | 11.000 | 11.000 | 11.000 |
| Sorbitol, 70% | 41.407 | 40.007 | 40.007 | 40.007 | 40.007 | 40.007 | 40.007 | 40.007 |
| Deionized Water | 20.200 | 20.000 | 20.000 | 20.000 | 20.000 | 19.800 | 20.000 | 20.000 |
| Carbowax 600 | 3.000 | 3.000 | 3.000 | 3.000 | 3.000 | 3.000 | 3.000 | 3.000 |
| CMC-7MXF | 1.100 | 1.200 | 1.200 | 1.200 | 1.200 | 1.400 | 1.200 | 1.200 |
| Tetrasodium Pyrophosphate | 0.500 | 0.500 | 0.500 | 0.500 | 0.500 | 0.500 | 0.500 | 0.500 |
| Sodium Saccharin | 0.200 | 0.200 | 0.200 | 0.200 | 0.200 | 0.200 | 0.200 | 0.200 |
| Sodium Fluoride | 0.243 | 0.243 | 0.243 | 0.243 | 0.243 | 0.243 | 0.243 | 0.243 |
| Zeodent 165 Silica thickener | 0 | 1.5 | 1.5 | 1.5 | 1.5 | 1.5 | 1.5 | 1.5 |
| Example 1 abrasive | 20.000 | | | | | | | |
| Example 2 abrasive | | 20.000 | | | | | | |
| Example 3 abrasive | | | 20.000 | | | | | |
| Example 4 abrasive | | | | 20.000 | | | | |
| Example 5 abrasive | | | | | 20.000 | | | |
| Ex. A boehmite | | | | | | 20.000 | | |
| Ex. B Boehmite | | | | | | | 20.000 | |
| Zeodent 115 silica abrasive | | | | | | | | 20.000 |
| Titanium dioxide | 0.500 | 0.500 | 0.500 | 0.500 | 0.500 | 0.500 | 0.500 | 0.500 |
| Sodium Lauryl Sulfate | 1.200 | 1.200 | 1.200 | 1.200 | 1.200 | 1.200 | 1.200 | 1.200 |
| Flavor | 0.650 | 0.650 | 0.650 | 0.650 | 0.650 | 0.650 | 0.650 | 0.650 |

The results of the fluoride availability, RDA and PCR measurements are set forth in Table VI, below.

TABLE VI

| | Toothpaste Composition Number | | | | | | | |
|---|---|---|---|---|---|---|---|---|
| | 1 | 2 | 3 | 4 | 5 | 6 | 7 | 8 |
| RDA | 66 | 71 | 100 | 111 | 72 | 43 | 46 | 69 |
| PCR | 80 | 94 | — | — | 100 | 75 | 84 | 77 |
| % Fluoride Availability (F/A) | | | | | | | | |
| 1 week, 80° F. | 104 | 94 | 104 | 101 | 99 | 102 | 97 | 104 |
| 1 week, 120° F. | 100 | 75 | 97 | 99 | 94 | 93 | 86 | 101 |
| 6 weeks, 80° F. | 103 | 86 | 97 | 93 | 96 | 104 | 100 | 102 |
| 6 weeks, 120° F. | 97 | 49 | 74 | 83 | 93 | 85 | 59 | 98 |
| 9 weeks, 80° F. | 103 | — | 92 | 88 | 94 | 92 | — | 102 |
| 9 weeks, 120° F. | 97 | — | 90 | 87 | 87 | 70 | — | 95 |

Toothpaste Compositions 6, 7 and 8 were control compositions. Toothpaste Composition 6 contained the Example A untreated boehmite, which was used as the substrate for the silica-coated boehmite used in Toothpaste Composition 1. Toothpaste Composition 7 contained the untreated boehmite of Example B, which was used as the substrate for the silica-coated boehmite used in Toothpaste Compositions 2, 3, and 4. Toothpaste Composition 8 contained Zeodent® 115, a prior art abrasive silica.

Toothpaste Composition 8, containing a commercial silica abrasive sets the bar for the experimental abrasives with a reasonably low RDA of about 70 at 20% toothpaste loading while having a reasonable high PCR value and excellent fluoride availability. The toothpaste compositions containing uncoated boehmite have low abrasivity (RDA) values, which results in low PCR values.

Toothpaste Compositions 1–5 contained silica-coated boehmite prepared in Examples 1–5, which were prepared according to the present invention. Compositions 1, 2 and 5 in particular had RDA and fluoride availability values comparable to those of composition 8, which contained Zeodent 115 silica, but compsotions 1, 2 and 5 had surprisingly higher PCR values than the PCR value of Composition 8.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

What is claimed is:

1. A composite material comprising a boehmite substrate coated with a precipitated silica, the composite material having an Einlehner abrasion value of about 15 mg lost/100,000 revolutions to about 30 mg lost/100,000 revolutions, and a BET specific surface area of from 1 $m^2/g$ to 50 $m^2/g$, such that the composite material has a % silica coating parameter value of 5% to 50%, based on the ratio of the weight of the precipitated silica to the total weight of the boehmite and precipitated silica.

2. The composite material according to claim 1, wherein the composite material has a median particle size of about 1 μm to about 20 μm.

3. The composite material according to claim 1, wherein the composite material has a median particle size of 1 μm to 1 μm.

4. The composite material according to claim 1, wherein the boehmite substrate has a median diameter of 1 μm to 20 μm.

5. The composite material according to claim 1, wherein the boehmite substrate has a median diameter of 1 μm to 5 μm.

6. The composite material according to claim 1, wherein the boehmite substrate has an Einlehner abrasion value of about 10 mg lost/100,000 revolutions to about 65 mg lost/100,000 revolutions.

7. The composite material according to claim 1, wherein the composite material has a BET surface area of 1 $m^2/g$ to 10 $m^2/g$.

8. The composite material according to claim 1, wherein the % silica coating value is between 15% to 40%, based on the ratio of the weight of the precipitated silica to the total weight of the boehmite and silica.

9. The composite material according to claim 1, wherein the composite material has a % CPC compatibility value of greater than about 40%.

10. The composite material according to claim 1, wherein the composite material has a % CPC compatibility value of greater than about 55%.

11. The composite material according to claim 1, wherein the composite material has a % CPC compatibility value of greater than about 75%.

12. The composite material according to claim 1, wherein the composite material has a fluoride compatibility value of greater than about 40%.

13. The composite material according to claim 1, wherein the composite material has a fluoride compatibility value of greater than about 80%.

14. The composite material according to claim 1, wherein the composite material has a CPC compatibility value of greater than about 40% and a fluoride value compatibility of greater than about 40%.

15. The composite material according to claim 1, wherein the composite material has a CPC compatibility value of greater than about 70% and a fluoride compatibility value of greater than about 80%.

16. A dentifrice containing a composite material comprising a boehmite substrate coated with a precipitated silica, the composite material having a BET specific surface area of from 1 $m^2/g$ to 50 $m^2/g$, such that the composite material has a % silica coating parameter value of 5% to 50%, based on the ratio of the weight of the precipitated silica to the total weight of the boehmite and precipitated silica, and wherein the dentifrice PCR/RDA ratio is greater than 1.2.

17. The dentifrice according to claim 16, comprising about 10% to about 35% by weight of the composite material based on the weight of the dentifrice.

18. The dentifrice according to claim 1, wherein the dentifrice PCR/RDA ratio is about 1.2 to about 1.5.

19. The dentifrice according to claim 1, wherein the dentifrice RDA value is greater than 60.

20. The dentifrice according to claim 1, further comprising one or more ingredients selected from the group consisting of abrasives, other thickeners, humectants, antibacterial agents, fluorides, flavors, sweeteners, and surfactants.

21. A method of forming a composite material that includes forming boehmite particles by adding aluminum trihydrate to an aqueous solution and then heating the aluminum trihydrate-containing aqueous solution, under a pressure of about 190 psi to 250 psi to form the boehmite particles, while simultaneously adding an acid to the aqueous solution containing alkali metal silicate, thereby depositing silica, which has a BET specific surface area of from 1 $m^2/g$ to 50 $m^2/g$, onto the boehmite particles to form a silica-treated boehmite composite material; the composite material having a % silica coating parameter value of 5% to 50%, based on the ratio of the weight of the precipitated silica to the total weight of the boehmite and precipitated silica.

* * * * *